(12) United States Patent
Hennessy

(10) Patent No.: US 8,913,790 B2
(45) Date of Patent: Dec. 16, 2014

(54) SYSTEM AND METHOD FOR ANALYZING THREE-DIMENSIONAL (3D) MEDIA CONTENT

(71) Applicant: TandemLaunch Technologies Inc., Westmount (CA)

(72) Inventor: Craig Adam Hennessy, Westmount, CA (US)

(73) Assignee: Mirametrix Inc., Westmount (CA)

( * ) Notice: Subject to any disclaimer, the term of this patent is extended or adjusted under 35 U.S.C. 154(b) by 132 days.

(21) Appl. No.: 13/764,397

(22) Filed: Feb. 11, 2013

(65) Prior Publication Data

US 2013/0156265 A1    Jun. 20, 2013

Related U.S. Application Data

(63) Continuation of application No. PCT/CA2011/000923, filed on Aug. 16, 2011.

(60) Provisional application No. 61/373,974, filed on Aug. 16, 2010.

(51) Int. Cl.
| | |
|---|---|
| *G06K 9/00* | (2006.01) |
| *H04N 13/04* | (2006.01) |
| *A61B 3/113* | (2006.01) |
| *G06F 3/01* | (2006.01) |
| *A61B 3/14* | (2006.01) |

(52) U.S. Cl.
CPC ........ *G06K 9/00597* (2013.01); *H04N 13/0484* (2013.01); *A61B 3/113* (2013.01); *G06F 3/013* (2013.01)
USPC ............................ 382/103; 382/291; 351/208

(58) Field of Classification Search
CPC .................................... G06K 9/00; A61B 3/14
USPC ......... 382/100, 103, 106–107, 117, 154, 162, 382/168, 173, 181, 232, 254, 274–276, 291, 382/305, 312; 351/208, 246
See application file for complete search history.

(56) References Cited

U.S. PATENT DOCUMENTS 7,029,121 B2 *   4/2006   Edwards ........................ 351/246
2004/0156020 A1   8/2004   Edwards (Continued)

OTHER PUBLICATIONS

El Hamad, Adel; Search Report from corresponding PCT Application No. PCT/CA2011/000923; search completed Dec. 7, 2012.

*Primary Examiner* — Seyed Azarian
(74) *Attorney, Agent, or Firm* — Brett J. Slaney; Blake, Cassels & Graydon LLP

(57) ABSTRACT

A system and method are provided that use point of gaze information to determine what portions of 3D media content are actually being viewed to enable a 3D media content viewing experience to be improved. Tracking eye movements of viewers to obtain such point of gaze information are used to control characteristics of the 3D media content during consumption of that media, and/or to improve or otherwise adjust or refine the 3D media content during creation thereof by a media content provider. Outputs may be generated to illustrate what in the 3D media content was viewed at incorrect depths. Such outputs may then be used in subsequent or offline analysis, e.g., by editors for media content providers when generating the 3D media itself, in order to gauge the 3D effects. A quality metric can be computed based on the point of gaze information, which can be used to analyze the interactions between viewers and the 3D media content being displayed. The quality metric may also be calibrated in order to accommodate offsets and other factors and/or to allow for aggregation of results obtained for multiple viewers.

24 Claims, 19 Drawing Sheets

(56) References Cited

U.S. PATENT DOCUMENTS

| | | | |
|---|---|---|---|
| 2006/0110008 A1* | 5/2006 | Vertegaal et al. | 382/103 |
| 2006/0210111 A1* | 9/2006 | Cleveland et al. | 382/103 |
| 2007/0279590 A1* | 12/2007 | Ebisawa | 351/208 |
| 2008/0181452 A1* | 7/2008 | Kwon et al. | 382/103 |

* cited by examiner

SYSTEM AND METHOD FOR ANALYZING THREE-DIMENSIONAL (3D) MEDIA CONTENT

CROSS-REFERENCE TO RELATED APPLICATIONS

This application is a continuation of International PCT Application No. PCT/CA2011/000923 filed on Aug. 16, 2011, which claims priority from U.S. Provisional Patent Application No. 61/373,974 filed on Aug. 16, 2010, both incorporated herein by reference.

TECHNICAL FIELD

The following relates to systems and methods for analyzing and displaying 3D media content.

DESCRIPTION OF THE RELATED ART

Eye-tracking systems have been used to track the motion of a viewer's eyes and consequently the point of gaze of the viewer. An example of an eye tracking system can be found, for example, in U.S. Pat. No. 4,950,069 filed Nov. 4, 1988 and entitled "Eye Movement Detector with Improved Calibration and Speed". The point of gaze is most commonly tracked on a two-dimensional (2D) surface such as a computer, television (TV), or any other 2D display that displays media content. In addition, recent advances in eye-trackers have enabled the ability to track the point of gaze on 3D displays and even in real-world 3D space.

Having knowledge of where a viewer is looking on a display can provide behavioral insight into the viewer's cognitive processes while viewing the media of interest. Where the viewer is looking is often closely tied to what the user is thinking. With eye gaze information, it is possible to tell what region of the media caught the user's attention first, what the user spent the longest time looking at, the order in which different regions were viewed, the regions that were never seen by the viewer, etc. Examples of systems that use eye-tracking for the analysis of 2D content include U.S. Pat. No. 6,601,021 filed Dec. 8, 2000 and entitled "System and Method for Analyzing Eyetracker Data"; and U.S. Pat. No. 7,029,121 filed Feb. 4, 2004 and entitled "Techniques for Facilitating Use of Eye Tracking Data".

BRIEF DESCRIPTION OF THE DRAWINGS

Embodiments will now be described by way of example only with reference to the appended drawings wherein.

DETAILED DESCRIPTION

Figure 1:
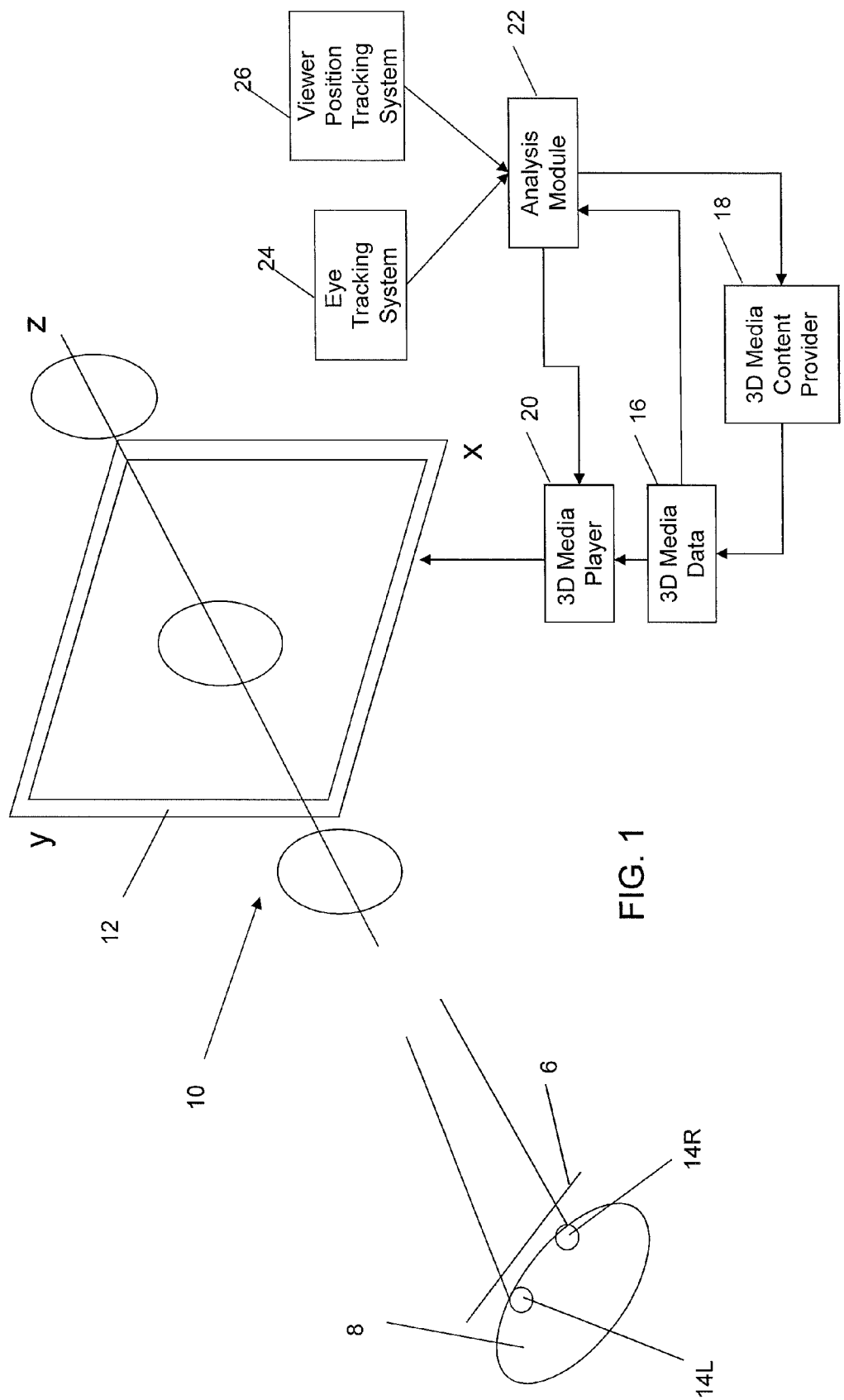
FIG. 1 is a schematic diagram illustrating an example of three dimensional (3D) media content being displayed and an analysis system for tracking a viewer's interactions with the 3D media content.

It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practised without these specific details. In other instances, well-known methods, procedures and components have not been described in detail so as not to obscure the example embodiments described herein. Also, the description is not to be considered as limiting the scope of the example embodiments described herein.

While eye tracking has been used for the analysis of 2D content for several years, eye tracking technology is also applicable to 3D content, which is finding increasing popularity with mainstream audiences. Content in 3D is developed by creating media for the left and right eye views. Multi-view cameras can be used to film in 3D, while digital media may be rendered directly for the left and right eyes based on a given ocular separation (typically estimated at 7 cm). A variety of methods may be used to display 3D content. For example, passive methods such as those using red-cyan and polarized glasses, may be used to split the left and right eye views. Active techniques may also be used, such as techniques that use liquid crystal display (LCD) shutter glasses with alternating video frames for the left and right eyes. More recently, autostereoscopic displays show 3D content without the need for glasses, using methods such as lenticular and parallax barrier screens. Heads-up displays may also be used to show 3D content by having two separate displays, one for each of the left and right eyes.

In addition to where the viewer is looking on the media, binocular eye gaze tracking can provide significant insight into the impression of depth through tracking the vergence (converging point of the left and right eye) when looking at media displayed at differing depths. The quality of the depth effect, however, is difficult to determine unless it can be tested and quantified with human viewers.

Depth perception involves binocular cues such as stereopis and convergence, as well as monocular cues such as accommodation, object size, and occlusion. With binocular eye tracking it is possible to gain insight into the quality of the 3D media displayed by tracking the convergence of the viewer's point of gaze.

It has been found that by using point of gaze information to determine what portions of 3D media content are actually being viewed, a 3D media content viewing experience can be improved. Tracking eye movements of viewers to obtain such point of gaze information can be used to not only control characteristics of the 3D media content during consumption of that media, but also to improve or otherwise adjust or refine the 3D media content during creation thereof by a media content provider. Outputs may be generated to illustrate what and where in the 3D media content was viewed and in which areas were the depth effects incorrect. Such outputs may then be used in subsequent or offline analyses, e.g., by editors for media content providers when generating the 3D media itself, in order to gauge the effectiveness of the 3D media content and 3D effects.

It has also been found that a quality metric can be computed based on the point of gaze information, which can be used to analyze the interactions between viewers and the 3D media content being displayed. The quality metric may also be calibrated in order to accommodate offsets and other factors and/or to allow for aggregation of results obtained for multiple viewers.

Turning now to FIG. 1, the display of 3D media content 10 on a display screen 12 is shown. It can be appreciated that the display screen 12 in this example includes a 2D display capable of rendering media content in 3D, and the display used may be a stand-alone unit such as a television or computer monitor or an embedded screen in, for example, a portable gaming device, smart phone, laptop or tablet computer, or any other device utilizing a 3D capable 2D display. As shown in FIG. 1, the display screen 12 may be given a set of reference axes, in this example wherein the x-axis extends horizontally from left to right (from the viewer's perspective), the y-axis extends vertically from bottom to top, and the z-axis extends perpendicularly through the display screen 12 from the viewer. The 3D media content may include any type of content, such as text, images, video, etc.; provided using any suitable medium such as television, web (wired and wireless), etc.

In the example shown in FIG. 1, the 3D media content 10 is being viewed by a viewer 8 having a left eye 14L and a right eye 14R. The viewer 8, if required, utilizes 3D glasses, heads-up display or other eyewear 6 for achieving a 3D effect. The 3D media content 10 is generated, distributed or otherwise provided as 3D media data 16 by a 3D media content provider 18. For example, the 3D media data 16 may be stored to a physical medium such as a DVD, or provided as streaming data by, for example, a server. The 3D media data 16 is used to display the 3D media content 10 on the display screen 12 using a 3D media player 20. The 3D media data 16 may include any visual scene which is viewed in 3D, where the left and right eyes of the viewer see the scene from different points of view such that the impression of depth is given. The left and right eye views of the 3D media may be provided through the use of shutter glasses, polarized glasses, anaglyph glasses, auto stereoscopic displays, random dot stereograms, or any other such technique. 3D media content may include still images (pictures, magazines, etc.), video sequences (movies, TV, etc), computer-generated imagery (video games, computing interfaces, etc), among others.

It can be appreciated that the 3D media player 20 and 3D media data 16 are shown separate from the display screen 12 for ease of illustration and such components may be part of the same device.

An analysis module 22 is also shown in FIG. 1, which may be used to gather eye tracking data from an eye tracking system 24 and/or viewer position data from a viewer position tracking system 26, and to determine characteristics of the 3D media data 16 to analyze and control the output of the 3D media content 10 and/or display information associated with the viewer's interactions with the 3D media content 10. For example, as will be described by way of example below, data provided by the eye tracking system 24 can be used to perform a gaze depth analysis for adjusting the depth of objects in the 3D media content 10.

A binocular eye tracking system 24 may be used to perform a gaze depth analysis on the 3D media content 10 being displayed. Such an eye tracking system 24 should be configured to accurately identify the location of the point of gaze for both the left eye 14L and right eye 14R of the viewer 8 on the display screen 12 (270, 275—see also FIG. 6), regardless of the technology used to display the 3D media. As will be explained by way of example below, the left and right POG 270, 275 can be used to estimate a 3D POG (308—see also FIG. 10). If the eye tracking system 24 is capable of computing a 3D POG directly, the 3D POG provides an estimate of the gaze depth. An example of a method and system capable of computing a 3D POG 308 directly is PCT Patent Application No. PCT/CA2008/000987 filed May 23, 2008 and entitled "Methods and Apparatus for Estimating Point-of-Gaze in Three Dimensions", published as WO 2008/141460, the entire contents of which are incorporated herein by reference.

It can be appreciated that eye tracking systems 24 that use active infrared lighting provide the ability to image the eyes 14L, 14R through eyewear 6 such as polarized or LCD shutter glasses, as these glasses often limit the light entering and reflecting off the eyes 14L, 14R. Alternatively, visible light eye tracking systems 24 may be used if there is sufficient ambient light for the eye tracking system 24 to observe the eyes 14L, 14R. If shutter glasses are used (where the left and right eyes are alternately blocked), the opening and closing of an eye-tracker camera shutter may be synchronized with the toggling rate of the shutter glasses. If synchronized directly, each tracker image frame will record the left eye 14L or right eye 14R. If synchronized with a percent duty cycle time offset (for example 50%), each camera image will be exposed to a percentage of the open shutter time for both the left eye 14L and right eye 14R, allowing both eyes 14L, 14R to be imaged at the same time. A similar effect could be achieved by operating the shutter glasses at higher toggling rates than the eye-tracker shutter. For example, running the eye tracking system 24 at 60 Hz and the shutter glasses at 120 Hz would result in imaging both the left eye 14L and right eye 14R in a single camera image. In the event that one eye (14L or 14R) is missing in the eye tracking system's camera image for a short duration, the last known good eye position or point of gaze position may be used for that eye to allow for continued operation. If the eye (14L or 14R) is lost for a larger duration, the ability to estimate gaze depth may be lost.

It can be appreciated that the eye tracking system 24, viewer tracking system 26, and analysis module 22 are shown as separate components and independent of the 3D media player 20, 3D media data 16, and display screen 12 for illustrative purposes only. Any one or more of these components may be included in a same device or system. For example, a home theatre system may include the analysis module 22 in a 3D media player 20 with an eye tracking system 24 supported by or integrated with a TV which includes the display screen 12. Similarly, a single portable electronic device such as a smart phone may include all of the components shown in FIG. 1 including, optionally, the 3D media content provider 18 (e.g. if viewer/user is creating content using their device).

Figure 2:
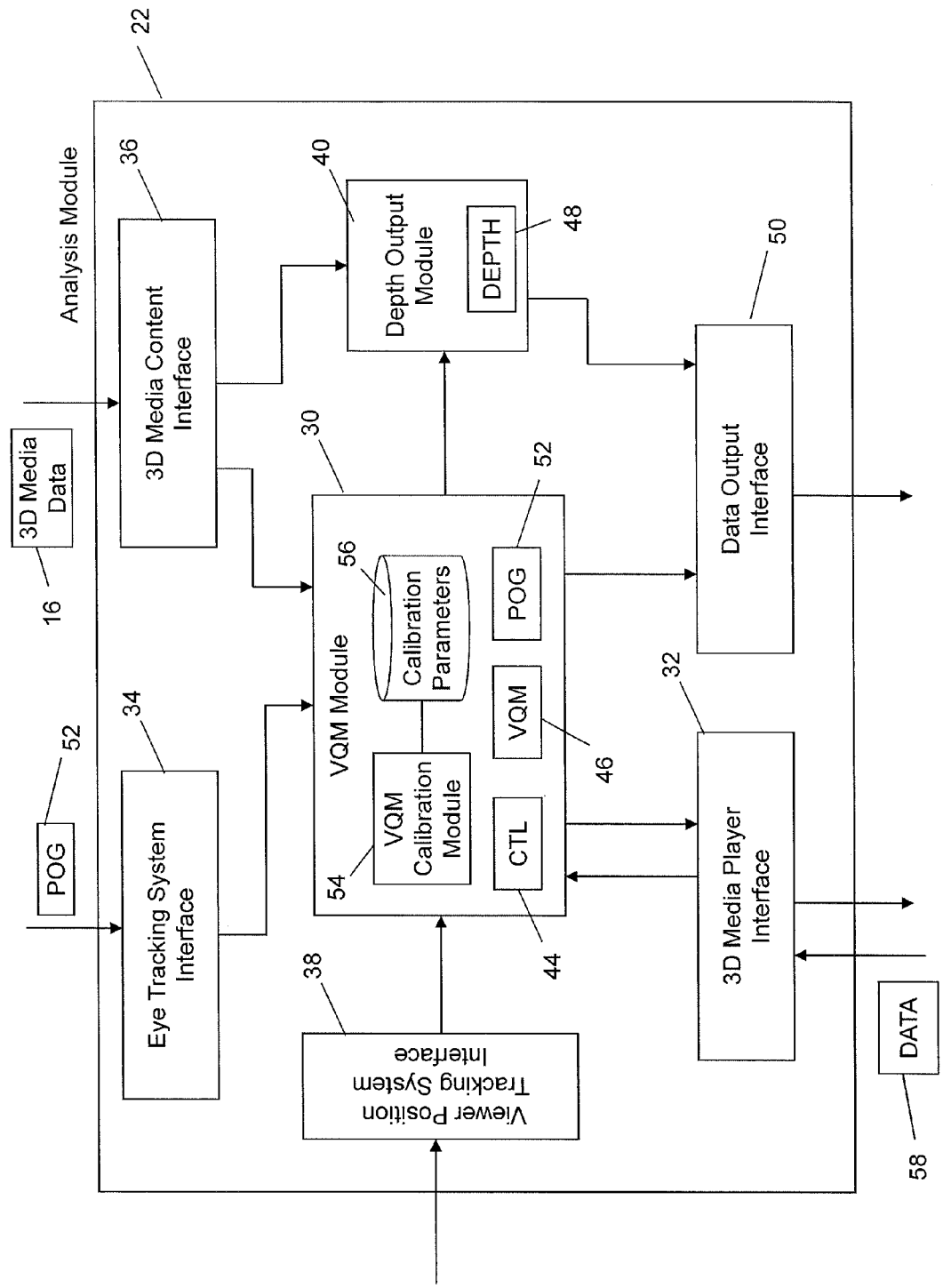
FIG. 2 is a block diagram illustrating an example of a configuration for an analysis module used in an analysis system for tracking a viewer's interactions with 3D media content.

FIG. 2 illustrates an example of a configuration for the analysis module 22. To determine an estimated depth of gaze for a viewer 8, a vergence quality metric (VQM) module 30 is provided. As will be explained in greater detail below, the VQM 46 provides a relative measure of an estimated depth of gaze of the viewer 8 with respect to a reference point in the 3D media content 12. The VQM 46 can be computed using the left and right points of gaze on a 2D display, or a 3D POG 308 determined directly, provided by the eye tracking system 24. In either case, POG data 52 may be obtained by the VQM module 30 via an eye tracking system interface 34. The VQM module 30 may also be configured to analyze other data 58 provided by the 3D media player 20 via a 3D media player interface 32. In addition to the 3D Media 10 to display, the other data 58 can include, for example, temporal or spatial statistics related to the 3D media content 10, content-of-interest information which outline specific content in the media which may have significant interest (such as product placements), performance statistics related to playing the 3D media content 10 (e.g. where pauses, skips, rewind, fast-forward, etc. was performed), etc. The VQM module 30 may also generate a control instruction (CTL) 44 for controlling the output of the 3D media player 20 and send the control instruction 44, for example, to the 3D media player 20 using the 3D media player interface 32.

The VQM 46 generated by the VQM module 30 may also be provided as an output itself, e.g. to another system (not shown) such as a video editing monitor, using a data output interface 50, in order to enable the other system to perform an analysis of the 3D media content 10. The VQM 46 can also be provided to a depth output module 40 to enable the analysis module 22 to generate one or more numerical or visual depth outputs (DEPTH) 48. For example, numerical depth data, contour mappings, heat maps, content analyses, content of interest information, etc., can be generated to provide a visual output to a viewer, content provider, or both. The depth outputs 48 can also be provided to other systems using the data output interface 50. As shown in FIG. 2, the VQM module 30 may also have access to a 3D media content interface 36 for obtaining the 3D media data 16 or portions thereof, or otherwise interacting directly with the 3D media data 16 (e.g. to alter the 3D media data 16). In examples where the viewer's position with respect to the display screen 12 can be ascertained (e.g. if the analysis module 22 has access to data provided by a viewer position tracking system 26), a viewer position tracking system interface 38 may also be provided to enable the VQM module 30 to obtain viewer position data (not shown).

It can be appreciated that the viewer's position is typically relevant to auto-stereoscopic displays wherein the viewer does not need to wear special glasses. For example, the display screen 12 may use a barrier, or lenses to project different images to the left eye 14L and right eye 14R. This only works effectively if the eyes 14L, 14R are located at the appropriate position (sweet spot) where the system is projecting the left and right eye images to the left and right eyes. If you know where the eyes are, you can project the left and right eye images directly towards the true positions of the eyes with steerable lenses or other techniques.

It can also be appreciated that the interfaces 32, 34, 36, 38, and 50 shown in FIG. 2 may be any physical/wired or wireless connection or coupling.

Any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the analysis module 22, 3D media player 20, eye tracking system 24, viewer position tracking system 26, etc. (or other computing or control device that utilizes similar principles), or accessible or connectable thereto. Any application or module herein described may be implemented using computer readable/executable instructions that may be stored or otherwise held by such computer readable media.

Figure 3:
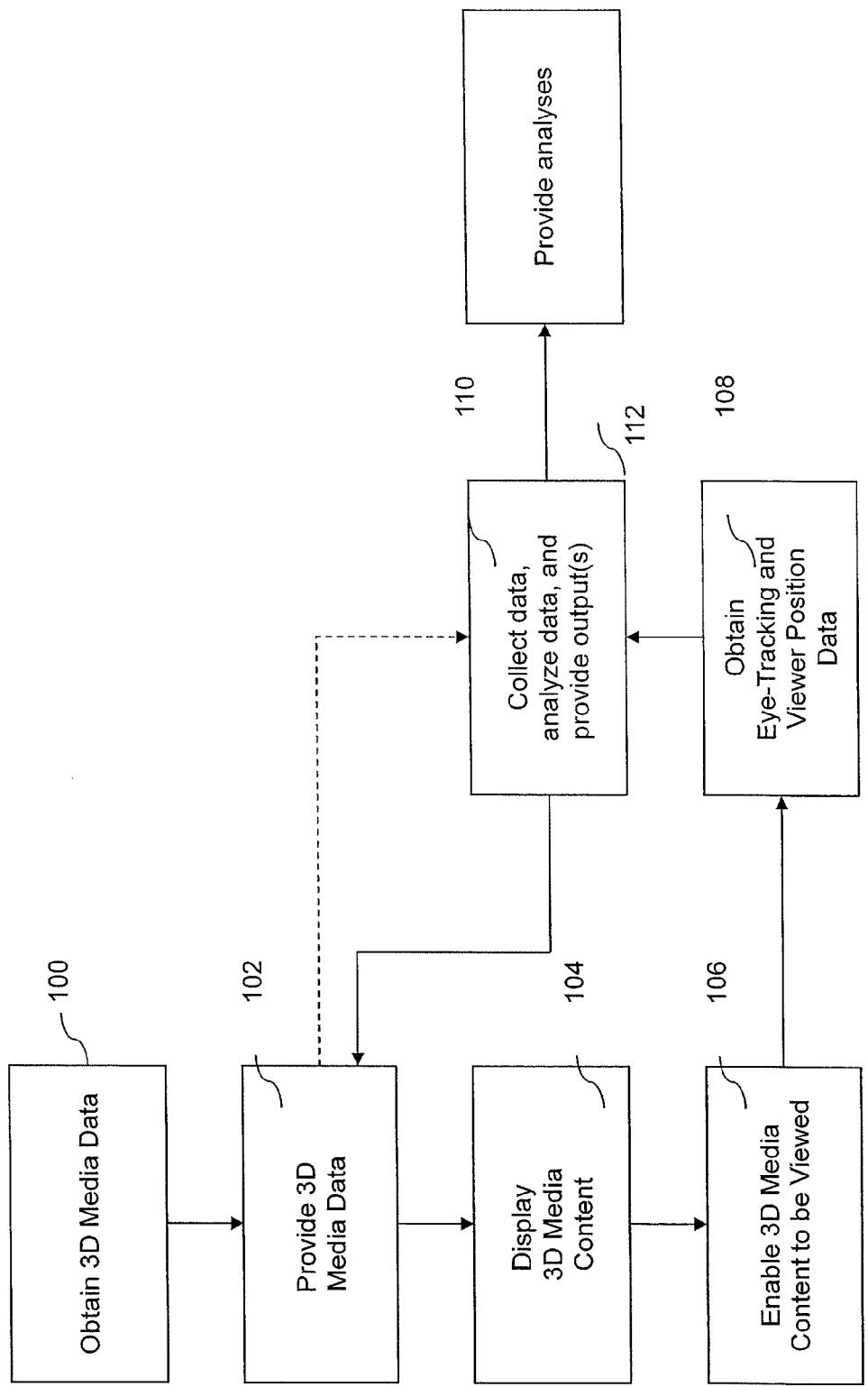
FIG. 3 is a flow chart illustrating an example of a set of computer executable operations that may be performed in analyzing a viewer's interactions with 3D media content and generating one or more outputs based on analyses.

FIG. 3 illustrates a set of computer executable operations that may be performed by the 3D media player 20, display screen 12, and eyewear 6 (and related media equipment) in playing 3D media content 10 for a viewer 8; and by the eye tracking system 24 and analysis module 22 in analyzing the viewer's interactions with the 3D media content 10, and generating one or more outputs related to same. At 100, the 3D media data 16 is obtained, e.g. from the 3D content provider 18, or a location in a memory (not shown). As discussed above, the 3D media data 16 may relate to text, images, video, web content, video games or other content that can be shown on the display screen 12 (e.g. stereoscopically or auto-stereoscopically). The 3D media data 16 is then provided at 102 to the display screen 12 and, in some embodiments, to the analysis module 22 (as shown by dashed lines in FIG. 3), and the 3D media content 10 displayed by the display screen 12 at 104. As discussed above, the 3D media content 10 may be displayed by any suitable device having a 3D compatible display screen 12, such as a television, computer monitor, portable device display, theater projector, portable projector, etc., that uses any one or more of a variety of technologies for presenting 3D media content 10. The display screen 12 and/or eyewear 6 enables the 3D media content 10 to be viewed by the viewer 8 at 106. For example, the display screen 12 may render a 3D image that can be viewed without eyewear 6 or may render separate images for the left eye 14L and right eye 14R that can be polarized by the eyewear 6 to perceive a 3D image.

Eye tracking and/or viewer position data are obtained at 108, e.g. by interfacing with the eye tracking system 24 and viewer position tracking system 26. The eye tracking system 24 provides POG data 52 such as the viewer's POG on the display screen 12 for each of the left eye 14L and right eye 14R, or by obtaining a depth measurement from a direct 3D POG computation. It can be appreciated that the eye tracking system 24 may also determine other information such as pupil dilation, fixations, saccades, eye positions and additional parameters of interest to an analysis. The eye tracking system 24 may also be equipped or programmed to track heart rate, perspiration, and other biometric measurements which can be used to estimate a viewer's emotional state and response to the content shown. The data obtained from the eye tracking system 24 and, if provided, details associated with the 3D media data 16 itself is collected and analyzed at 110. The results of the analysis can be used in providing (i.e. adjusting or modifying) the 3D media data 16 for display, and/or to present a numerical or visual analysis output at 112. As discussed above, the results of the analyses can be provided in various ways both using the display screen 12 or by providing the results to other systems such as video editing equipment.

Figure 4:
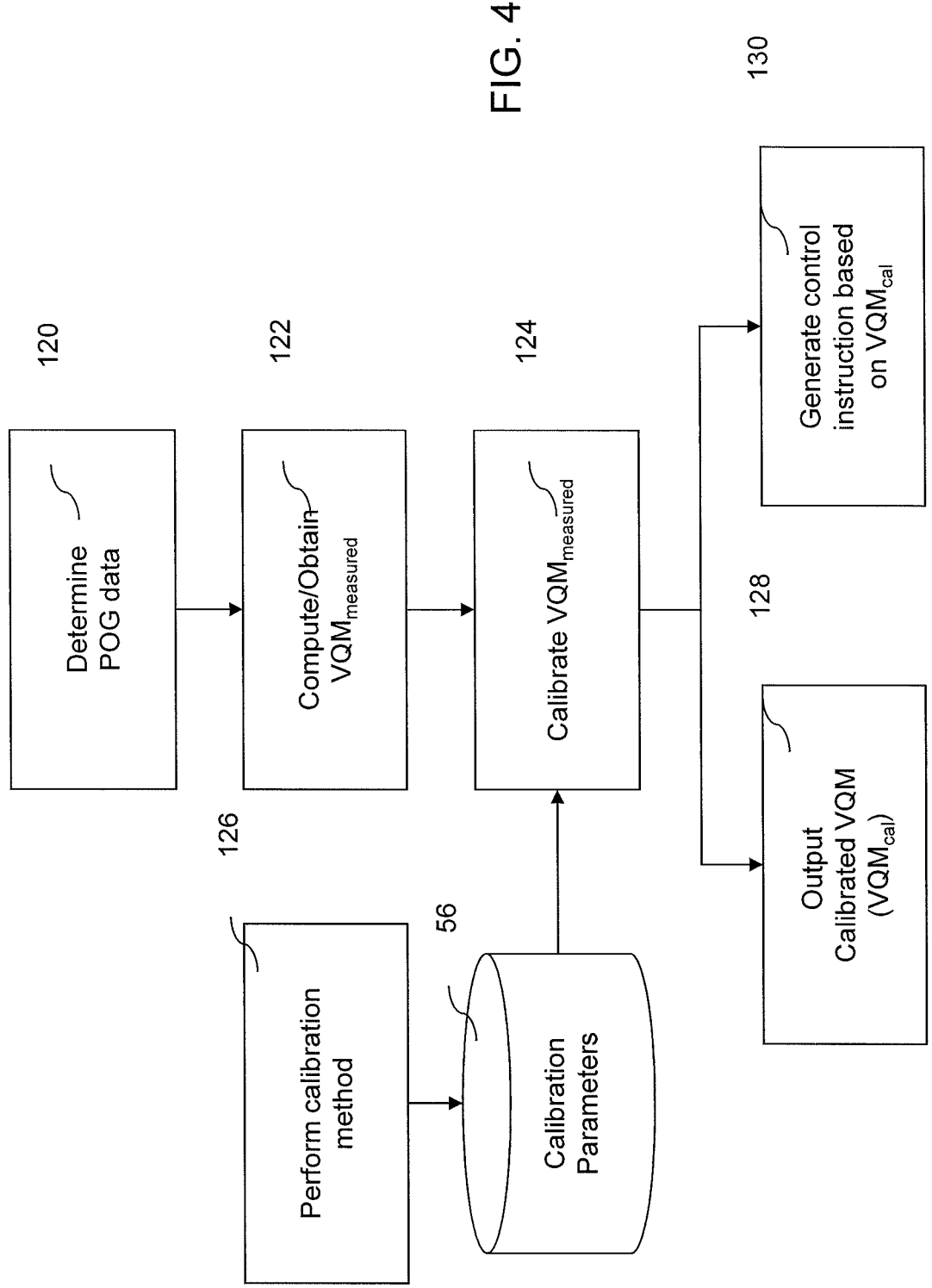
FIG. 4 is a flow chart illustrating an example of a set of computer executable operations that may be performed in generating and utilizing a calibrated vergence quality metric (VQM).

FIG. 4 illustrates a set of computer executable operations that may be performed by the VQM module 30 in computing or obtaining a VQM 46, calibrating the VQM 46, and outputting and/or generating a control instruction 44 based thereon. It can be appreciated that a measured VQM 46 may or may not require calibration and thus for simplicity, VQM 46 may refer to the value used in the particular application, e.g., either a measured VQM, namely $VQM_{measured}$ or a calibrated VQM, namely $VQM_{cal}$ generated from $VQM_{measured}$. The example shown in FIG. 4 assumes a calibration is performed for illustrative purposes. The VQM module 30 determines the POG data 52 at 120, and computes or otherwise obtains the $VQM_{measured}$ therefrom at 122. For example, if the eye tracking system 24 is capable of obtaining the 3D depth gaze directly, the provided measurement (e.g. in centimeters, pixels, etc.) is related to or otherwise converted to $VQM_{measured}$. The $VQM_{measured}$ is a relative measurement and thus may require calibration at 124 to correct for offsets and/or to allow for aggregation of information concerning multiple viewers. A calibration method may have been previously performed at 126, or may be performed at 126 immediately before or during the delivery of the 3D media content 10. The calibration method generates one or more calibration parameters 56, e.g., a function to be applied to a computed $VQM_{measured}$ or a look-up table to adjust the computed $VQM_{measured}$ based on a known relationship between the $VQM_{measured}$ and depth in order to obtain $VQM_{cal}$. As shown in FIG. 2, the VQM, may be provided as an output at 128, and a control instruction 44 may be generated based on the $VQM_{cal}$ at 130, e.g., to correct blur based on the detected depth of view.

For binocular eye tracking systems 24 that compute the POG for the left eye 14L and right eye 14R on a 2D display screen 12, the VQM 46 may be determined according to the relative positioning of the left and right points of gaze. Assuming the viewers eyes are horizontally displaced (i.e. the head is not tilted to the side), in this example, the VQM 46 is computed as the difference between the X-coordinates of the left and right eye points of gaze on a 2D display screen. When observing standard 2D media on a display, the left and right eyes typically converge to the same point and the VQM 46 would be zero, where:

$POG_l=(X_l,Y_l)$;

$POG_r=(X_r,Y_r)$; and $VQM=POG_{rx}-POG_{lx}=0$.

When 3D media content 10 is displayed, the eye tracking system 24 can determine not only where on the display screen 12 the viewer 8 was looking, but also the depth, by comparing the 2D left and right eye POG positions on the 2D display screen 12. If the 3D media content 10 is displayed or "drawn" with a depth further from the viewer 8 than the screen, the VQM 46 is >0. The larger the VQM 46, the further into the scene the viewer 8 is looking and the greater the perceived depth effect, where:

$VQM=POG_{rx}-POG_{lx}>0$.

When 3D media content 10 is displayed closer to the viewer 8 than the screen, the left and right eye points of gaze on the 2D display screen 12 cross and the VQM 46 becomes increasingly negative, where:

$VQM=POG_{rx}-POG_{lx}<0$.

Figure 5:
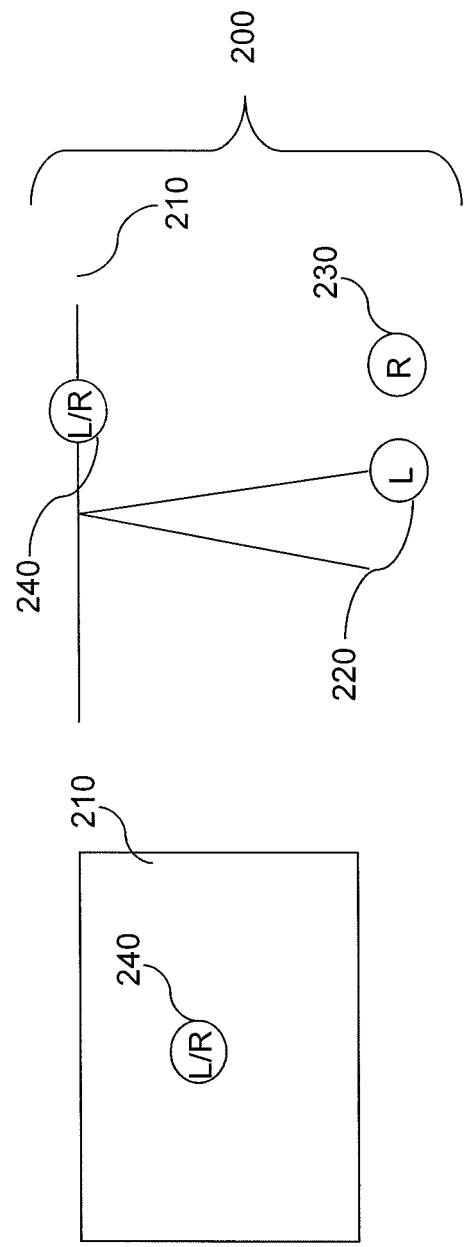
FIGS. 5 to 7 are schematic diagrams illustrating vergence points on, behind, and in front of a 2D display respectively.
Figure 6:
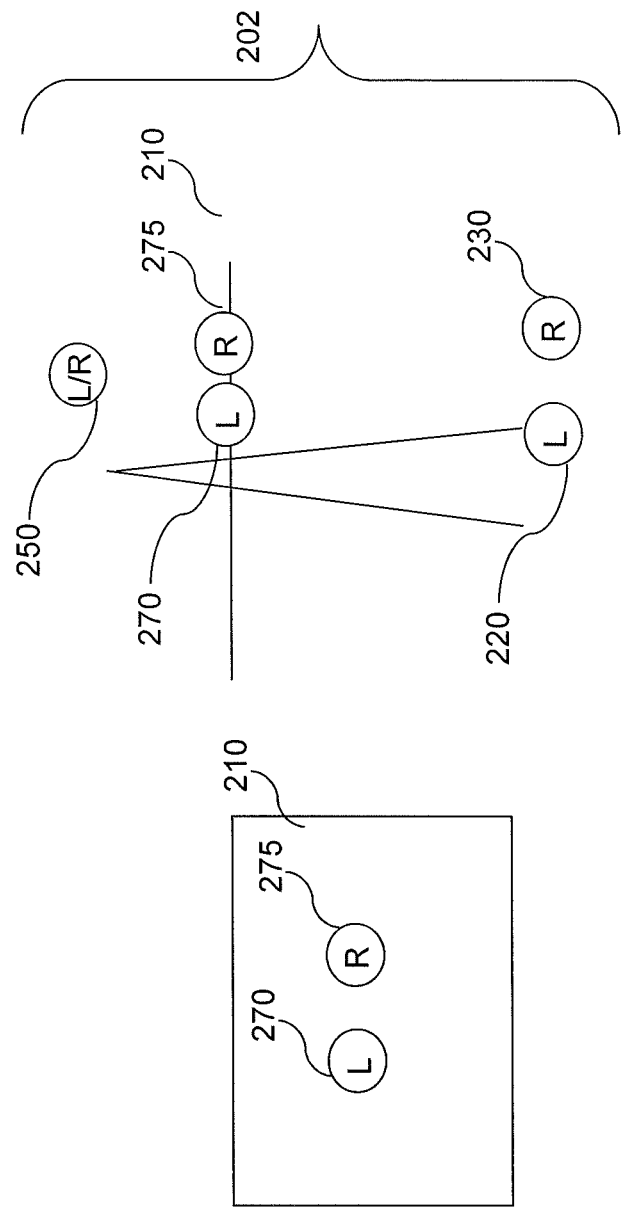
Figure 7:
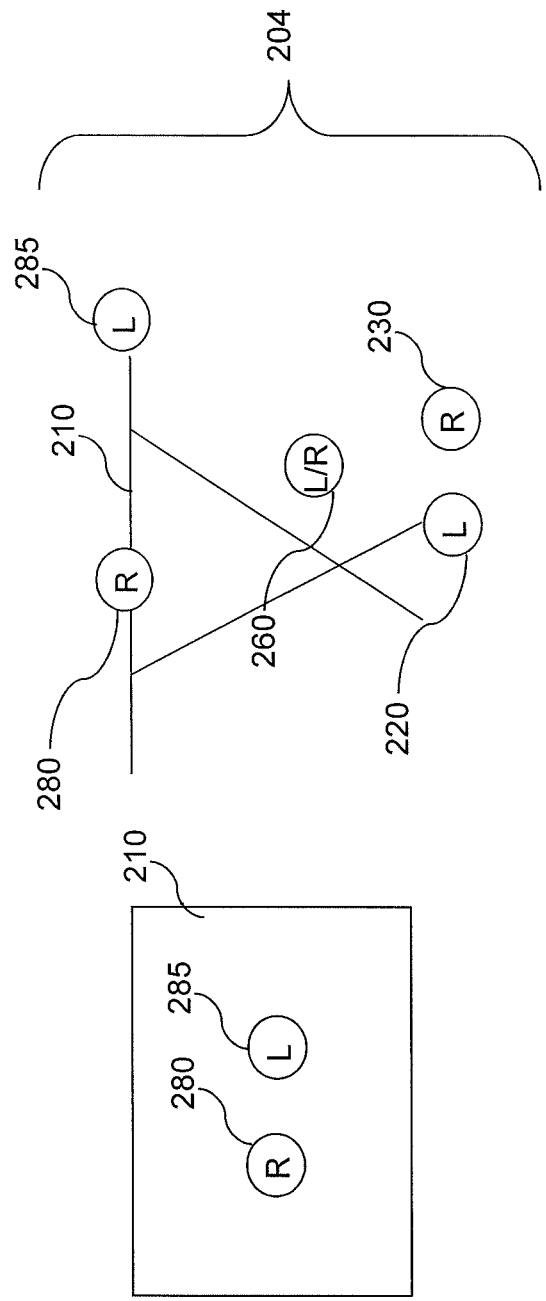

Turning to FIGS. 5 to 7, determining the vergence point on a 2D display screen 12 is illustrated with the corresponding point of gaze positions recorded by the eye tracking system 24 on the 2D display screen 12. The illustrations in FIGS. 5 to 7 are shown from two viewpoints, a front view shown on the left and a top view shown on the right. In FIG. 5, at 200, the left eye 14L and right eye 14R are observing a point of interest 240 on a plane 210 defined by the 2D display screen 12, in which both the left eye gaze 220 and right eye gaze 230 converge to the same point 240 on the plane 290 and the VQM=0.

In FIG. 6, at 202, the point of interest 250 is beyond the plane 210 of the display screen 12, which results in a VQM>0. In this example, the X-coordinate of the right point of gaze 275 is larger than the X coordinate of the left point of gaze 270.

In FIG. 7, at 204, the point of interest 260 is in front of the plane 210 of the display screen 12, which results in a VQM<0. In this example, the X-coordinate of the right point of gaze 280 is smaller than the X coordinate of the left point of gaze 285.

It may be noted that in the event the head is tilted, the VQM 46 can be computed as the distance between the left eye point of gaze and right eye point of gaze, (for example using the mathematical vector norm $\|POG_r-POG_l\|$) and the sign of the VQM taken to be positive if $POG_{rx}$ is to the right of $POG_{lx}$ (see FIG. 6) and negative if $POG_{rx}$ is to the left of $POG_{lx}$ (see FIG. 7) on the display. As many 3D displays require the eyes to be horizontal, the norm reduces to the horizontal subtraction described above. The sign of the VQM 46 was chosen to be positive behind the screen and negative closer to the viewer 8, however, if the subtraction was reversed (i.e. $POG_{lx}-POG_{rx}$) the VQM sign would be reversed and should be accounted for appropriately.

For binocular eye tracking systems 24 that compute the point-of-gaze in 3D, the VQM 46 can be obtained by determining the signed value of the Z-coordinate of a 3D point-of-gaze, where:

$VQM=POG_z$.

As discussed above, in the examples shown herein, the origin of the 3D POG coordinate system may be defined on the surface of the 2D display (typically the lower left corner), with the X-axis defined as the horizontal axis and increasing from left to right, the Y-axis defined as the vertical axis and is increasing from bottom to top, and the Z-axis defined perpendicular to the monitor display plane, increasing positively away from the viewer, and negatively towards the viewer.

When observing points on a 2D display, the VQM would be zero, where:

$VQM=POG_z=0$.

If the content is drawn with a depth further (behind) the screen, the VQM is >0, while content displayed closer to the viewer results in the VQM becoming increasingly negative, VQM<0.

It can be appreciated that the measurement used to compute the VQM 46 can be related in various ways to a reference point in the 3D media. For example, the VQM 46 can be measured in pixels or a percentage of the screen for a 2D eye tracking system 24, wherein the relative distance between the POGs 306L and 306R is determined, e.g., by comparing the X-coordinates or relative percentages of the screen from a reference point such as one edge of the display screen 12. For a 3D eye tracking system 24, the POG 308 may be measured in a real-world distance (e.g. centimeters). The number of pixels, percentage of the display screen 12, and real-world distance will typically not map directly to the distances in the actual 3D media content 10, since the 3D media content 10 may include various scenes of different scale, e.g., outer space, football game, living room in a sitcom, etc., where the depths depend on the content being shown. Moreover, the real-world depths may vary depending on the size of the display screen 12 (e.g. home theatre TV versus laptop versus smart phone, etc.) and the position of the viewer 8 in front of the screen. Therefore, the VQM 46 will likely need to be mapped to reference points specific to the 3D media content 10 in order to be able to compare the POG 308 to actual objects, to be able to use the VQM 46 to control the 3D media content 10, or to generate other outputs such as depth mappings (discussed in greater detail below). An example reference point could be a small shape, such as a cube or sphere, rendered at various positions and depths in front of the viewer.

Figure 8:
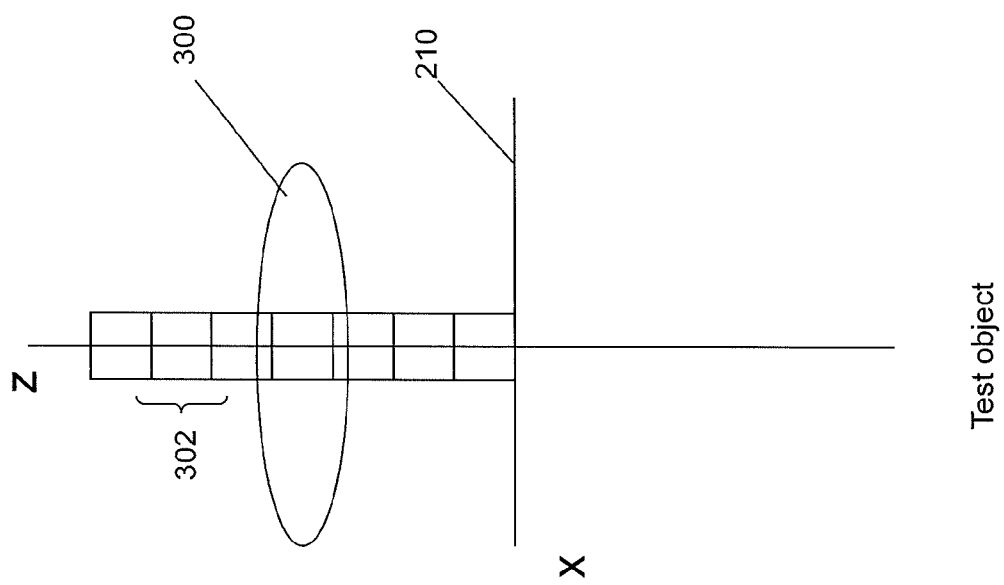
FIG. 8 is a schematic diagram illustrating the display of a calibration test object in a region behind a 2D display.
Figure 9:
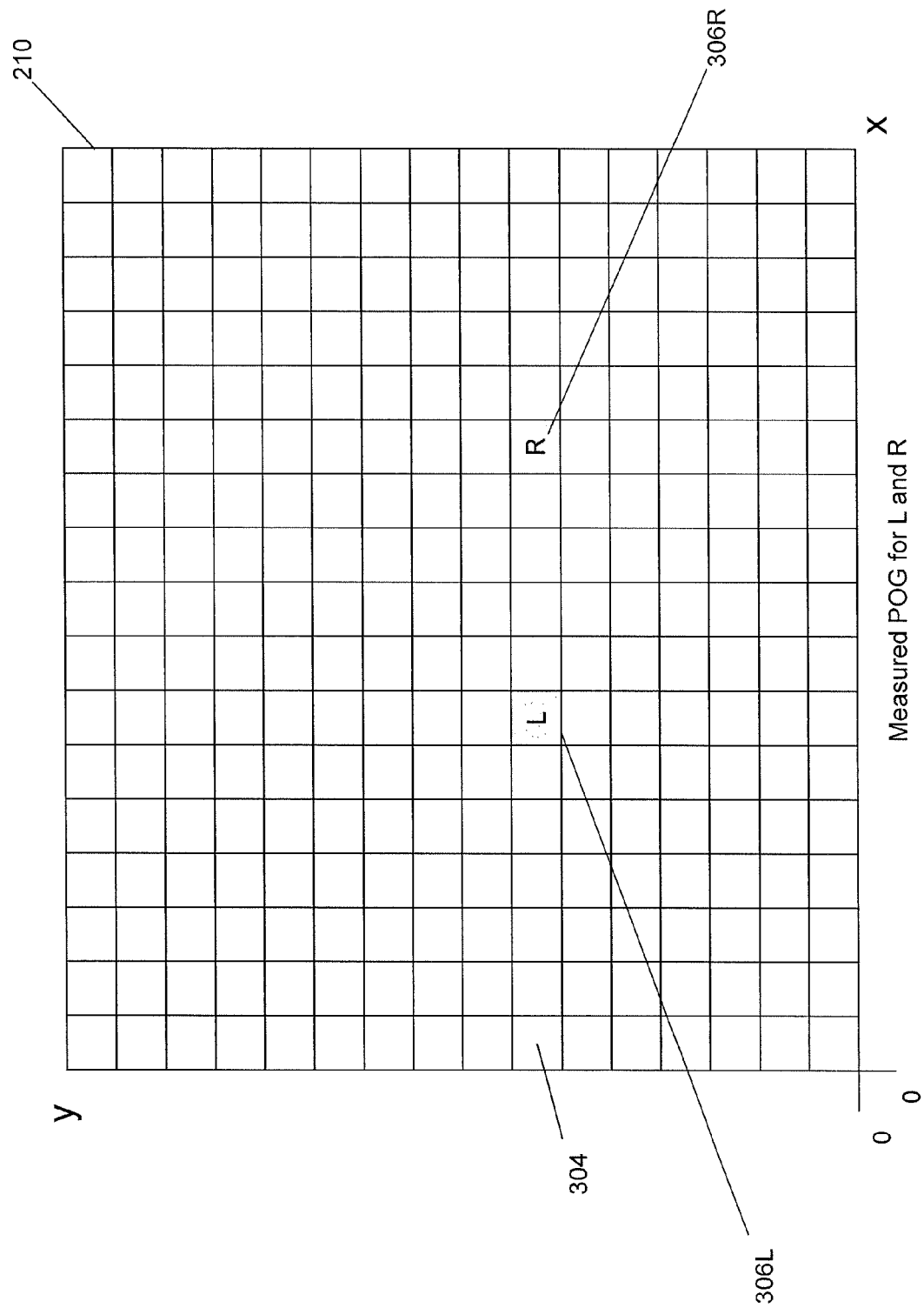
FIG. 9 is a schematic diagram illustrating left and right points of gaze on a 2D display.
Figure 10:
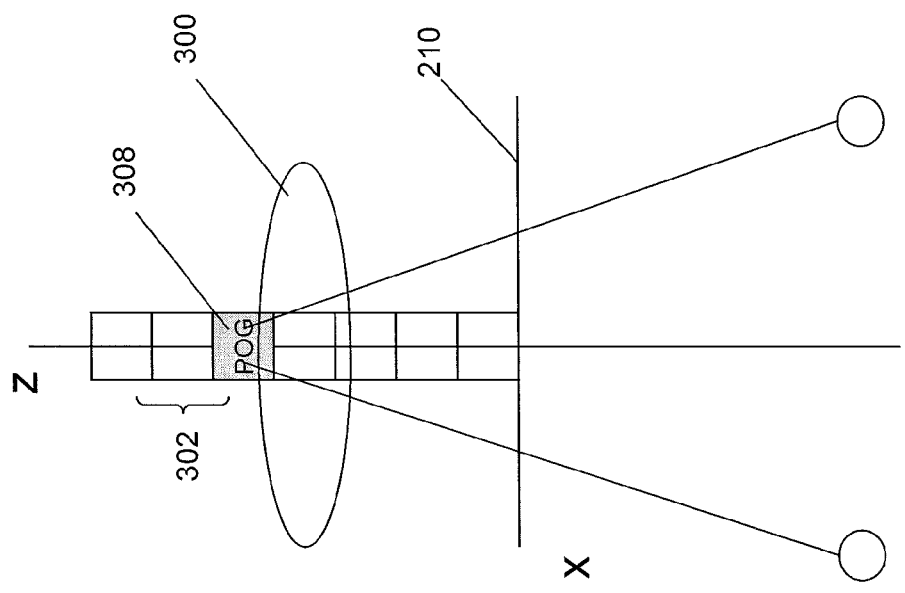
FIG. 10 is a schematic diagram illustrating a projected 3D point of gaze in relation to the calibration test object of FIG. 8.
Figure 12:
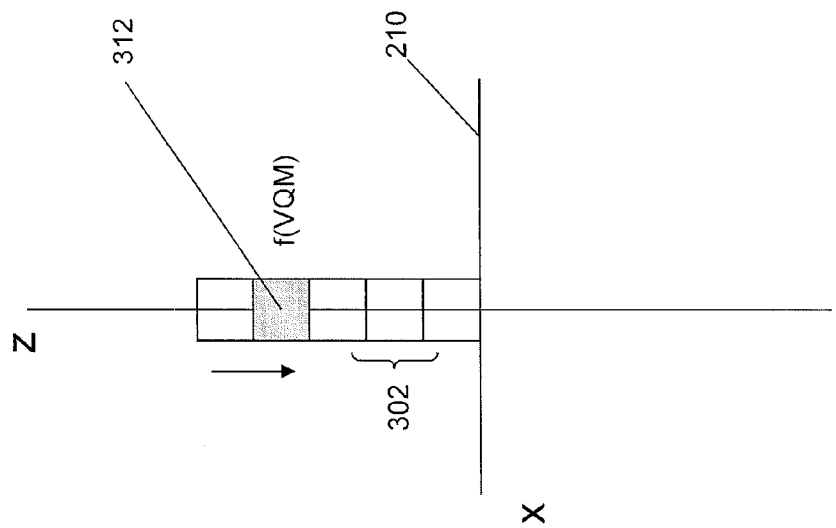
FIGS. 11 and 12 are schematic diagrams illustrating calibration of a VQM according to a predetermined function $f(VQM)$.
Figure 11:
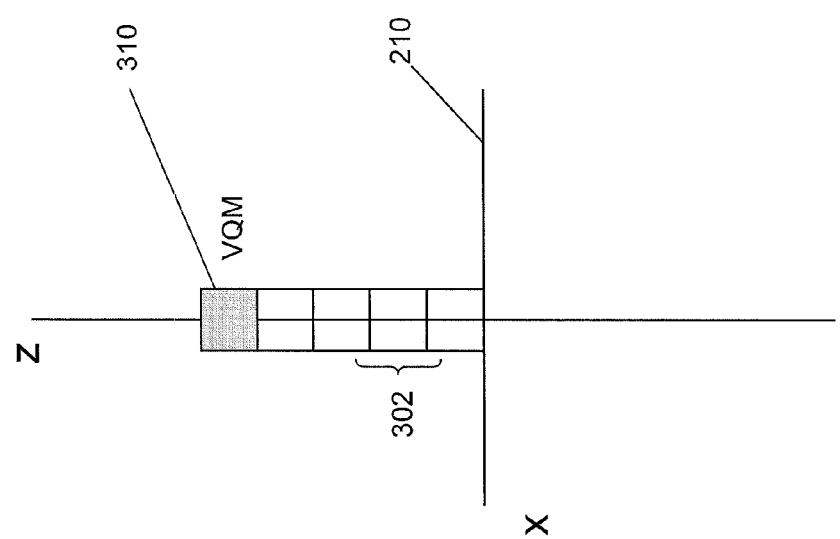

Since the VQM 46 is a relative measurement, the VQM 46 may require calibration to correct for offsets (such as when $POG_{rx}$ does not equal $POG_{lx}$ at zero depth), and to allow for aggregation of the results between multiple viewers. The calibration method performed at 126 may include displaying test objects 300 at known depths, e.g., as illustrated in FIG. 8. In the example shown in FIG. 8, a test object 300 is displayed behind the plane 210 of the display screen 12 at four (4) units of depth 302 beyond the plane 210. However, as illustrated in FIG. 9, in this example, the difference in X units 304 between the right POG 306R and the left POG 306L is five (5). In this example, this would translate to a POG depth 308 at 5 units of depth 302 as shown in FIG. 10. As such, the VQM 46 would not correspond to the 5 units measured using the X-coordinates in FIG. 9 and would need to be calibrated as shown in FIGS. 11 and 12. Note the units of depth may typically be in cm and units of distance between left and right point of gaze points in pixels, while in the example shown they are unit less.

In FIG. 11, the VQM 310 based on the data shown in FIG. 10 is at 5 units of depth 302. By applying a correction factor or otherwise computing a function of the VQM 46, namely $f(VQM)$, a calibrated VQM 312 can be determined as shown in FIG. 12. In this way, offsets that cause the eye tracking system 24 to perceive POGs 306L and 306R when the test object is drawn at 4 units of depth 302 can be determined and applied to compensate accordingly.

It can be appreciated that the calibration methods described herein may be applied to other metrics in addition to the VQM 46. In general therefore, a function of the POG information 52 obtained may be used to correct the computed depth measurement, e.g. $f(POG_l, POG_r)$ or $f(POG_{3D})$, etc.

Figure 13:
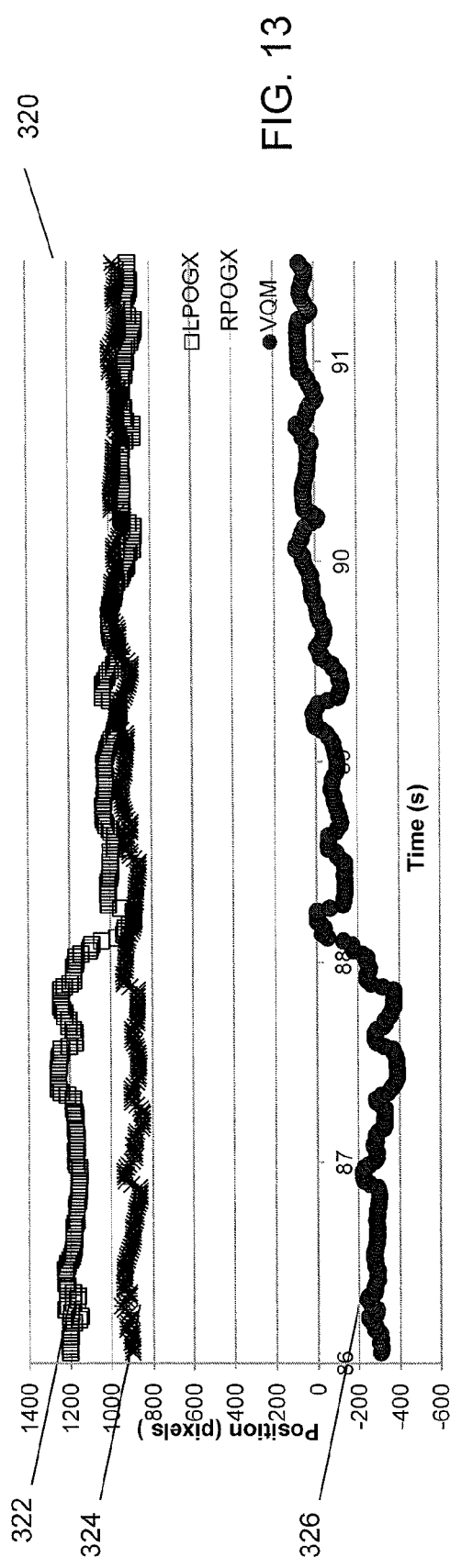
FIG. 13 is an example plot comparing left and right point of gaze data to a VQM.

Various calibration methods can be used to compensate for the factors affecting the 3D media content 10 in different applications. An example plot 320 is shown in FIG. 13 which illustrates an example calibration technique. In the example plot 320, the left $POG_X$ values (322) and right $POG_X$ values (324) (in pixels on the screen), and the VQM (326) is plotted over 5 seconds while looking at objects shown at 3 different real-world depths on a computer screen, +30 cm, 0 cm and −30 cm. The VQM 46 is approximately −290, −100 and 80 respectively in this example. In the example shown, real-world distances (e.g., cm measured by a ruler) were used. However, it can be appreciated that for various rendered 3D media, the units may be different.

An example calibration can involve looking at the $DIST_{NEAR}=-30$, $DIST_{ZERO}=0$ and $DIST_{FAR}=+30$ objects while measuring the respective VQM 46 values. In the data shown in FIG. 13, this would be, $VQM_{NEAR}=-290$, $VQM_{ZERO}=-100$, $VQM_{FAR}=80$.

For all subsequent VQM measurements, the following steps may be performed:
1) Remove the offset at zero depth: $VQM_{cal1}=VQM_{measured}-VQM_{ZERO}$;
2) If $VQM_{cal1}<0$ use: $VQM=(VQM_{measured}-VQM_{ZERO})*(DIST_{NEAR}/(VQM_{NEAR}-VQM_{ZERO}))$; and
3) If $VQM_{cal1}>0$ use: $VQM=(VQM_{measured}-VQM_{ZERO})*(DIST_{FAR}/(VQM_{FAR}-VQM_{ZERO}))$ Where $VQM_{cal1}$ is an intermediate value in the computation.

This example uses a linear mapping (of the form a*X+b). It can be appreciated that an inverse, power, exponential or other type of function may also result in an acceptable fit.

As is shown in FIG. 13, the VQM is computed over time such that the metric is continuously computed at each estimated point-of-gaze (POG(t)) resulting in VQM(t)). If the 3D media content 10 is static, such as an image, the VQM(t) will correspond to the location of the point-of-gaze POG(t) on the image. If the 3D media content 10 is dynamic, such as a video or computer game, the VQM(t) will correspond to both the location of the point-of-gaze POG(t) of the image and the video frame image or computer generated scene shown on the display at time T. For simplicity VQM as discussed herein may refer to any appropriate VQM value, whether or not time is a factor, e.g., VQM(t) as discussed above. Given the time sequence of the VQM(t), various filtering techniques may be employed to enhance the measurement depending on the desired application, for example finite-impulse response filtering may be used to smooth the estimated VQM values over time.

Figure 14:
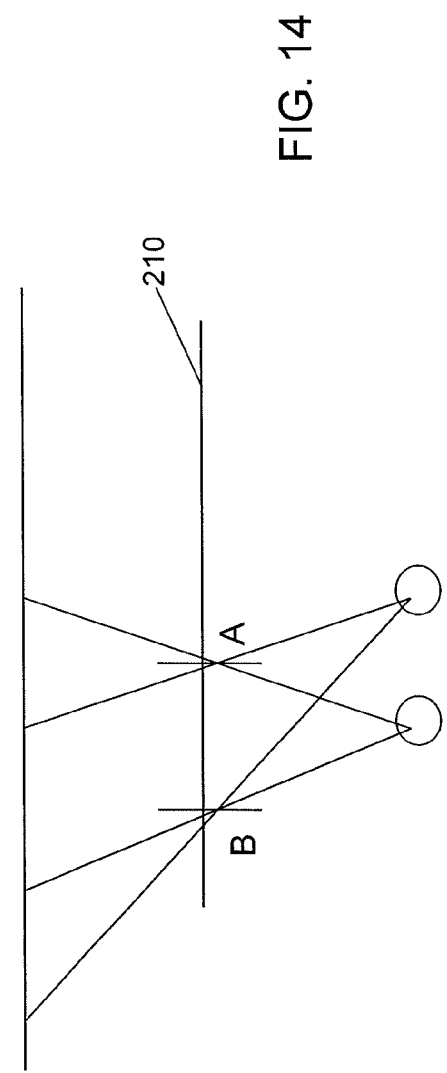
FIG. 14 is a diagram illustrating a non-linearity factor.

The calibration may be affected by various factors. Some factors include, without limitation: the quality of the eye tracking system 24 used, overall system noise, camera sensor noise, accuracy of the algorithms used, natural high speed movement of the eye and camera sampling rate, eye health, eye dominance, and non-linearity. Eye health may be affected by a cross-eyed condition among other things, wherein a dominant eye may be more significant while the other eye wanders. Non-linearity's when looking at the edge of the display screen 12 may also affect the calibration. For example, as shown in FIG. 14, when looking at point A, the left and right eye POG x-coordinates are equal distance apart, whereas looking at point B, this is no longer the case. Such an effect may be compensated for using the known locations of the eyes, the screen and the point of gaze estimates along with ray-tracing, or if the effect is minor, may simply be ignored. In particular, when a 3D POG measurement is used, the Z depth estimate is the same regardless of whether the viewer is looking at point A or B.

One way in which to obtain data for calibrating the VQM 46 may include showing a simple 3D scene in which test points (for example a small cube or sphere) are drawn at known depths that are: a) further than the screen, b) at the screen, and c) closer than screen with respect to the viewer 8.

The VQM 46 can be determined at each known position and a relationship computed (for example a linear function/quadradic function/lookup table), between the VQM 46 and depth, wherein as discussed above:

$VQM_{cal} = f(VQM)$, where $f$ is a function or look up table relationship determined through calibration.

Rather than prompting the viewer 8 to look at test points at known depths, calibration may be performed without conscious user interaction. Content can be displayed with known depths and known visual attraction (such as a soccer ball kicked out towards the viewer) in the course of regular viewing. The VQM 46 can then be calibrated with the assumption the viewer was looking at the object at the object depth.

To accommodate the event where the viewer was not looking at the object, the calibration process can also be performed multiple times to accumulate redundant measurements, since the calibration process in this example is unobtrusive to the viewer as they are not required to consciously participate. The collected measurements may then be filtered and sorted to identify the most frequent calibration measurement which is then selected as the correct value. Various filtering, sorting and selecting algorithms may be employed. For example, if 4 objects are shown over time at a similar depth, and the computed VQMs are $VQM_1=10$, $VQM_2=4$, $VQM_3=10$, $VQM_4=10$, then for that depth based on the highest frequency measure recorded the VQM 46 can be estimated to be 10.

Figure 15:
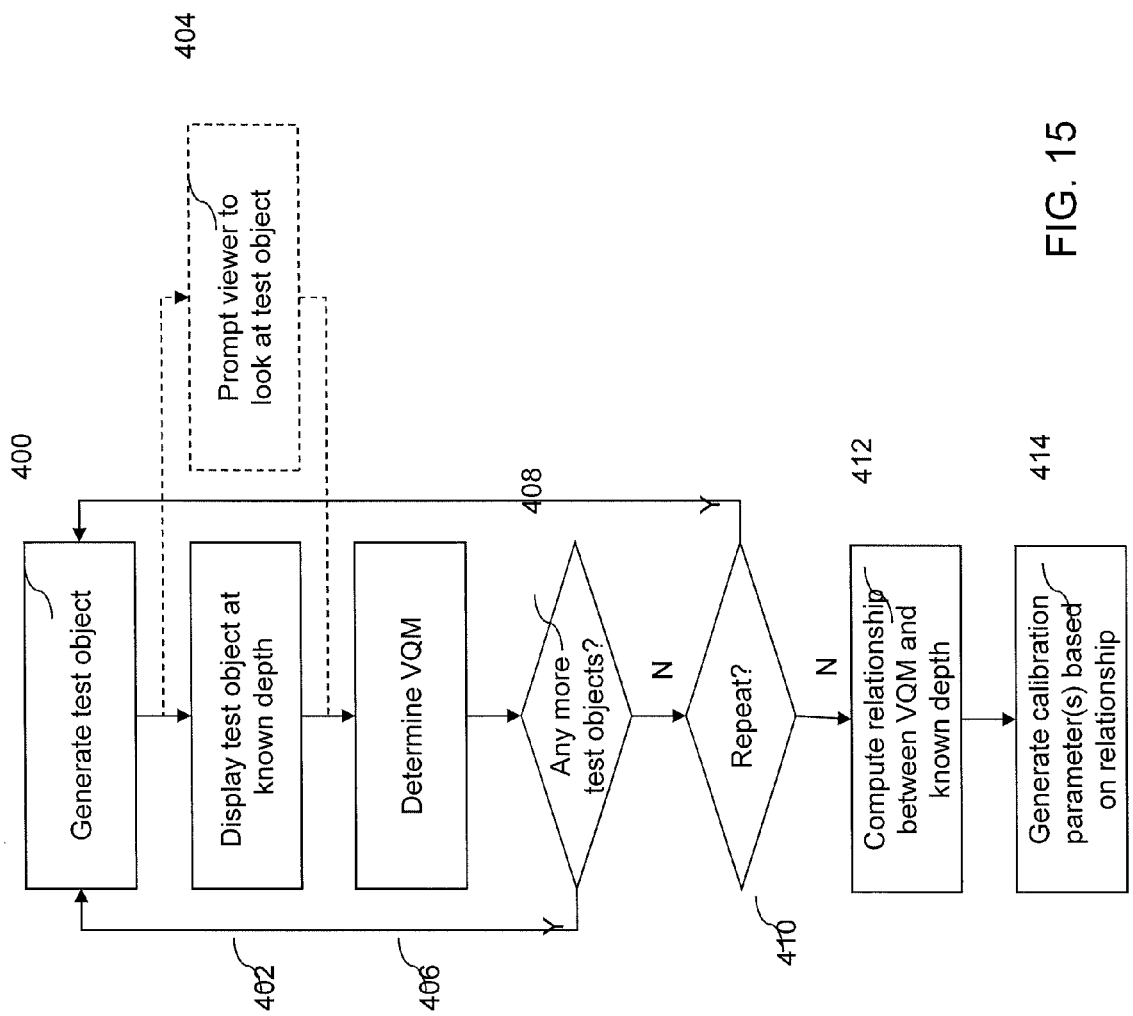
FIG. 15 is a flow chart illustrating an example of a set of computer executable operations that may be performed in performing a VQM calibration method.

FIG. 15 illustrates an example of a set of computer executable operations that may be performed by the VQM calibration module 54 in calibrating the VQM 46. At 400, a test object 300 is generated and the test object 300 is displayed at 402. The test object may be generated at run-time or previously and embedded in the 3D media. Display of the test object may include providing a prompt to the viewer 8 at 404 in order to have the viewer 8 look at the test object 300. However, as noted above, the calibration may be performed with or without the viewer's direct involvement and thus 404 is shown in dashed lines in FIG. 15. The VQM 46 may then be determined at 406, by obtaining POG data 52 from the eye tracking system 24. Multiple test objects 300 are displayed at different known depths and at 408, the VQM calibration module 54 determines if any more test objects 300 are to be displayed. If so, operations 400, 402, 404 (if required), and 406 are repeated. The process may also be repeated and at 410, the VQM calibration module 54 determines if another iteration is required. If so, operations 400, 402, 404 (if required), 406, and 408 are repeated. Once all of the test objects 300 have been displayed and the corresponding VQMs 46 computed, a relationship between the computed VQM 46 and the known depth is determined at 412 in order to generate one or more calibration parameters 56 at 414. As discussed above, the calibration parameters 56 may include a function $f(VQM)$, $f(POG_l, POG_r)$, $f(POG_{3D})$; a look up table; or any other mechanism to correct the computed VQM 46 or other depth measurement to account for factors pertinent to the particular application.

As shown in FIG. 4, the calibrated $VQM_{cal}$ may then be output for use by, for example, a 3D media player 20, 3D media content provider 18, or other system. The calibrated VQM 46 may also be used by the analysis module 22 to generate a control instruction 44 for adjusting the 3D media content 10 in various ways. Various other data may also be used in conjunction with the VQM 46, e.g., by obtaining viewer position data from a viewer position tracking system 26.

For example, knowledge of the viewer's position, such as seating position in a theater or the eye positions determined by the eye tracking system 24 when viewing a TV or other screen, can be used to determine the actual point of gaze using ray tracing from eye to POG position on the 2D display screen 12, and for computing the intersection point. For eye tracking systems 24 that provide eye positions, the 3D capable display screen 12 may incorporate this information to more appropriately render the 3D media content 10 based on the correct distance between the left eye 14L and right eye 14R. In addition, knowledge of the gaze position in depth may be used to develop human computer interfaces such as 3D pointing and gaze contingent rendering.

Figures 16, 17:
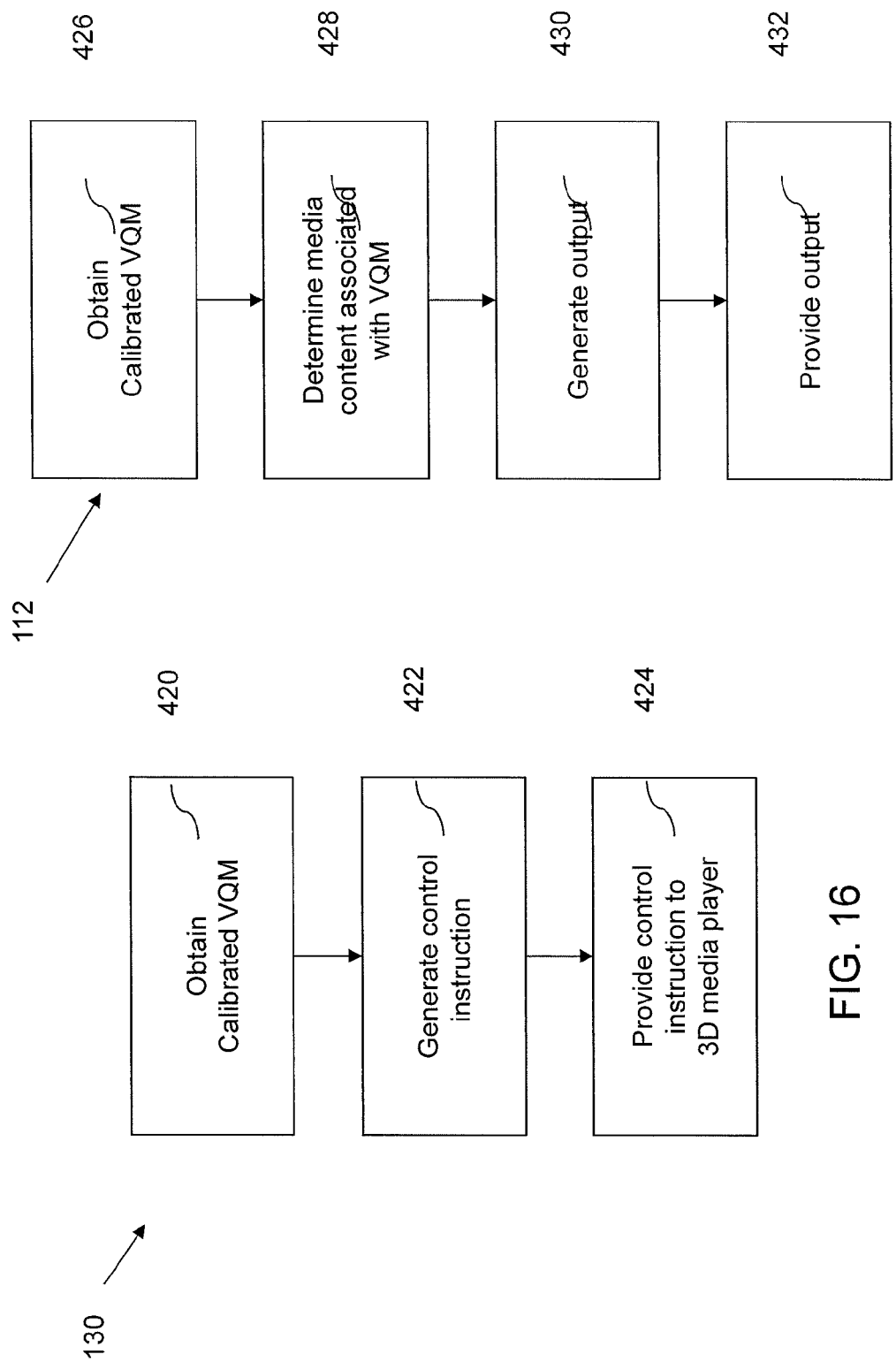
FIG. 16 is a flow chart illustrating an example of a set of computer executable operations that may be performed in providing a control instruction for a 3D media player based on an analysis of a viewer's interactions with 3D media content being played.
FIG. 17 is a flow chart illustrating an example of a set of computer executable operations that may be performed in generating an output comparing an observed VQM to depth data associated with 3D media content.

FIG. 16 illustrates a set of computer executable operations for generating a control instruction at 130 (see also FIG. 4), wherein the calibrated VQM 46 is obtained at 420, the control instruction 44 is generated at 422 based on the VQM 46, and the control instruction 44 is provided, in this example, to the 3D media player 20 at 424. The control instruction 44 may be generated to adjust or otherwise modify the 3D media content 10, e.g., to improve the viewing experience. For example, it is well known that not everyone can watch 3D media (estimates of up to 10% of the population have difficulty) and if poor correspondence between the displayed content and viewers gaze depth is determined, the depth effect could be reduced or even disabled, similar to the depth effect slider on portable gaming systems such as the Nintendo 3DS™.

Figure 19:
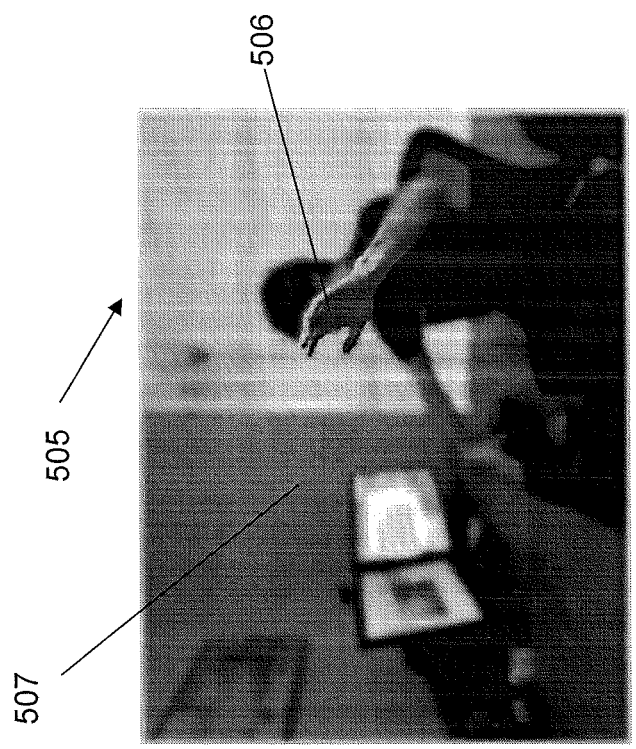
FIG. 19 is an illustration of a 2D image that has been adjusted according to an analysis of the 2D depth image in FIG. 18.
Figure 18:
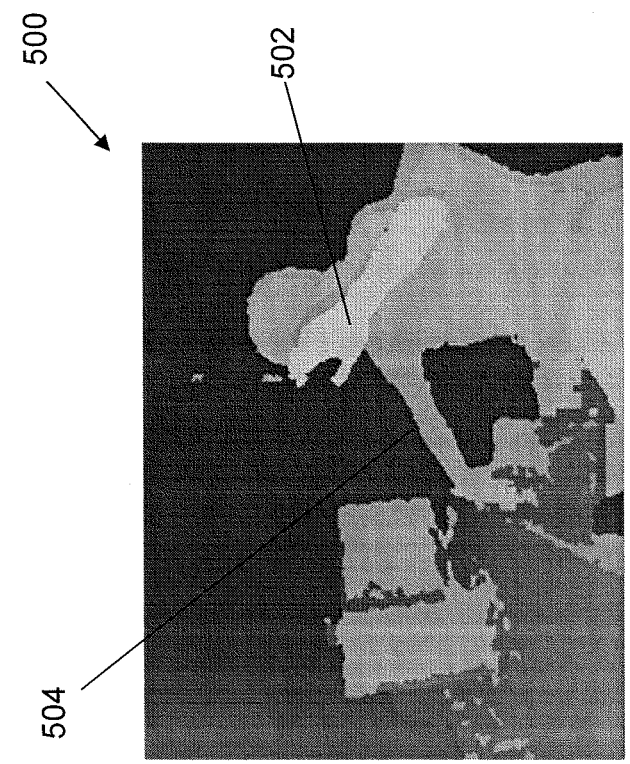
FIG. 18 is an illustration of a 2D depth image.

The 3D media player 20 can be configured to adjust the associated media content in real-time, i.e., as the media is being consumed. For a 3D scene, a depth image 500 as shown in FIG. 18 is used, wherein a grayscale image of the scene 505 shown in FIG. 19, is obtained or computed, with the intensity of objects being lower the further away they are in the scene 505. For example, the persons hand in the foreground 502 in FIG. 18 is lighter than the persons other arm 504 shown deeper in the scene 505. The analysis module 22 can therefore be used to track where on the 3D scene the viewer 8 is looking, with content at that depth in sharp focus and/or rendered at high resolution, and content away from that depth blurred and/or at lower resolution. For example, if a viewer was looking at the persons hand in the foreground, the hand would be rendered in focus 506 while the rest of the image is blurred 507.

For 3D media content 10 shown on a stereoscopic display screen 12, a three dimensional scene is rendered with objects in the foreground and background. When the viewer 8 looks at the foreground objects, and the 3D POG is closer to the viewer 8 at some arbitrary distance, the background objects are blurred. Such a technique may be used, for example in a video game where images are generated on-the-fly. It can be appreciated that burring may be performed by applying a Gaussian blur to an image or portion of the image, or any other suitable available technique.

While depth information for content that is rendered in real-time is easily determined (from the 3D models used to render the scene), for 3D media content 10 like a movie, a depth mapping may be needed, similar to FIG. 18. In this case the viewer depth measurements are compared against the depth map, while the 3D media is displayed to the viewer.

Human visual systems typically use various cues to determine the depth of an object. Monocular cues include motion parallax, depth from motion, perspective, relative size, familiar size, aerial perspective, accommodation, occlusion, etc., while binocular cues include stereopsis and convergence.

It has been found that in modern 3D capable display screens 12, most of these depth cues can be accurately simulated to provide a viewer with the perception of depth, with one exception, the accommodation of the eyes. Since the display screen 12 is actually a 2D surface, the natural blurring of a scene at depths further and nearer from the point of gaze is typically not represented, as the viewer 8 tends to be accommodating (focused) on the exact depth of the 2D display screen 12 at all times. This mismatch between accommodation and other visual depth cues may cause disorientation and discomfort that afflicts some viewers 8 when viewing 3D media content 10.

Figures 20, 21, 22:
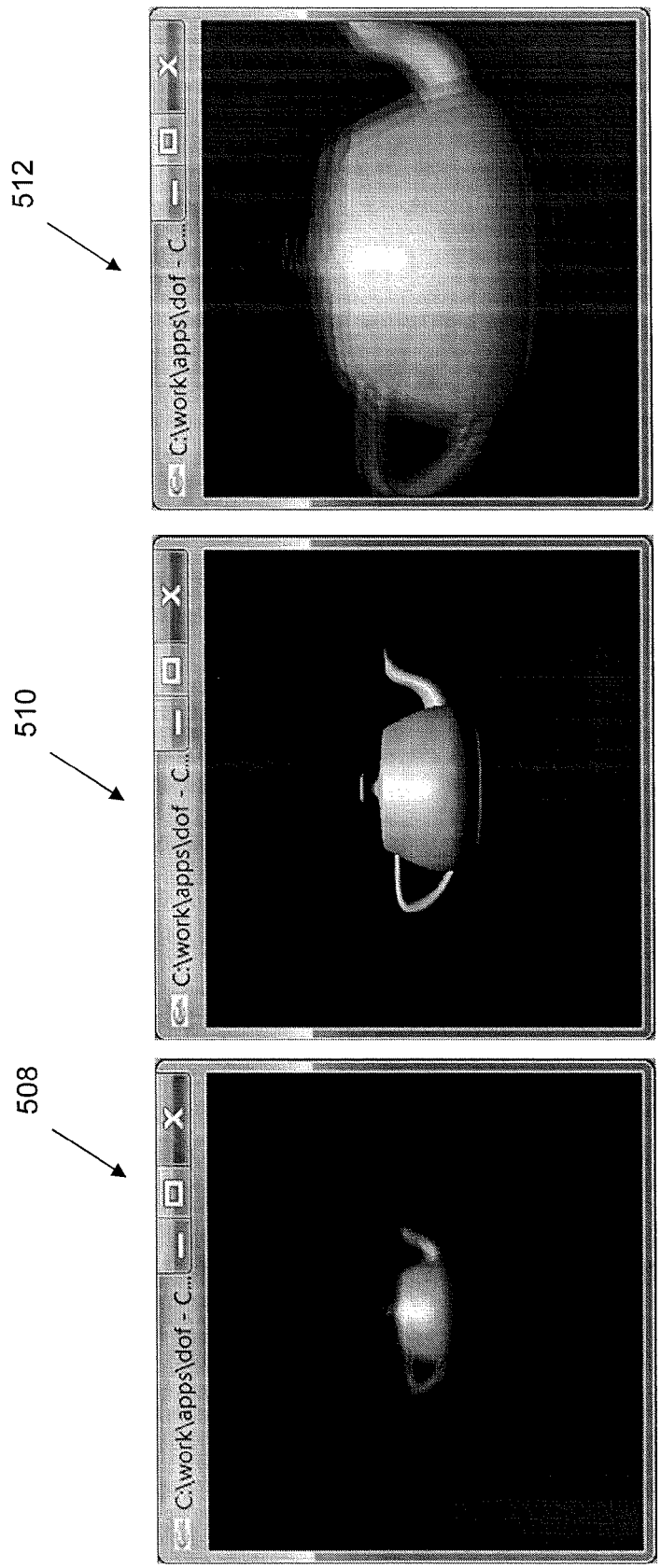
FIGS. 20 to 23 illustrate use of a 3D point of gaze depth estimation to blur near and far scenes to reduce visual discomfort with stereo displays.

Using the 3D POG and the VQM 46 computed by the analysis module 22, a control instruction 44 can be generated to have the scene defocused or blurred, based on the position of the 3D point of gaze on the display screen 12, and the relative depth of the scene at this gaze position. As shown in the computer generated image sequence of FIGS. 20 to 22, the same object (a teapot in this example) is rendered in a sequence from far to near, with the viewer's POG focused on the object when it was at the middle depth 510 of FIG. 21. Accordingly, at FIG. 21 the object is drawn in focus, while when rendered at the far depth 508 in FIG. 20 and the near depth 512 at FIG. 22, the object is blurred to simulate the viewer's true visual depth of field.

Figure 23:
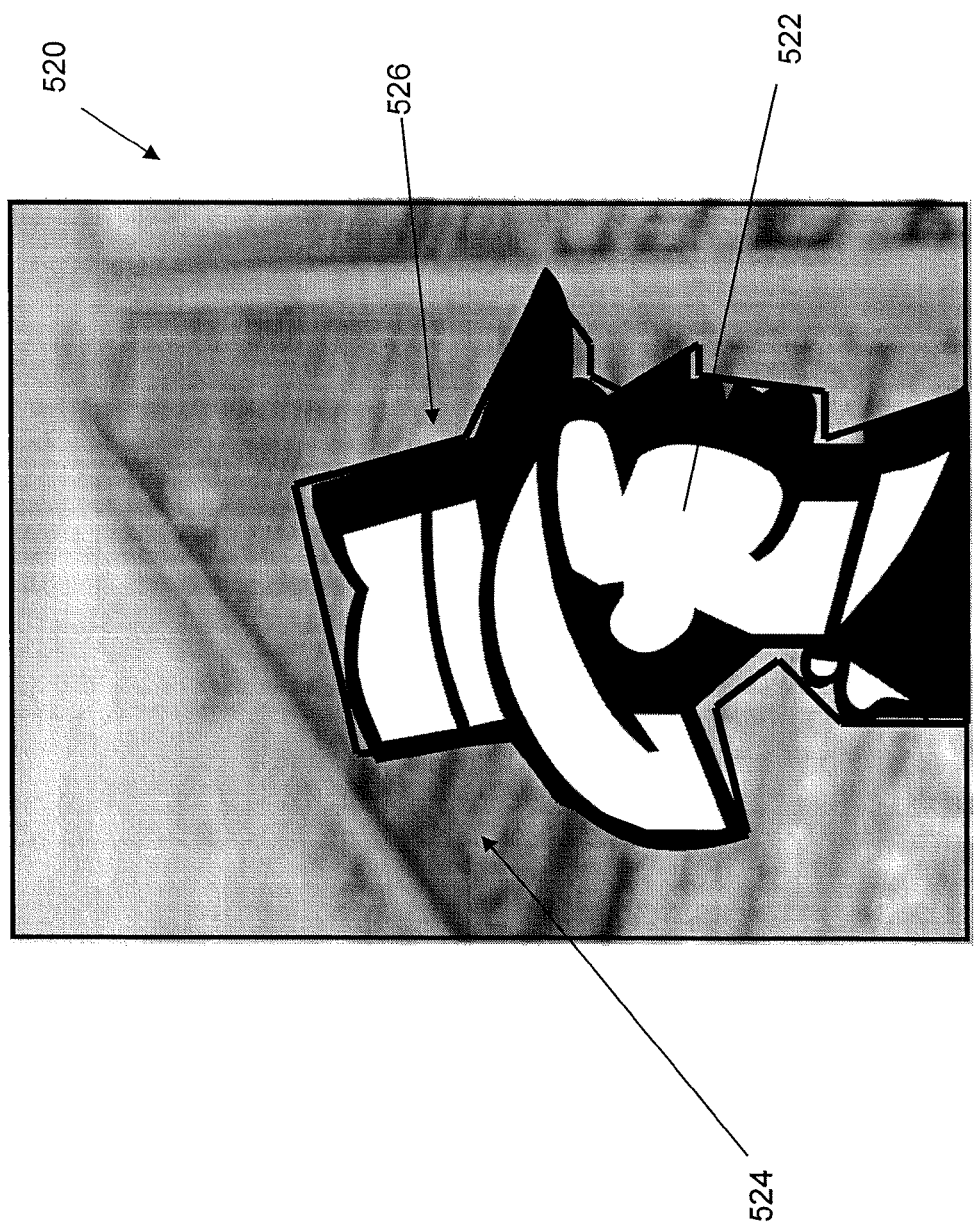

In another example, viewing the face of an actor 522 in a scene 520, may result in the actor being rendered with full clarity, while the background scene image 524 surrounding the actor 522 is defocused or blurred as shown in FIG. 23. If the viewer 8 then switches to viewing the background scene 524 (identified by an increase in depth of the 3D point of gaze) the actor 522 can then be blurred and the background scene 524 brought into sharper focus. To differentiate content such as 'actor' and 'background', a depth map may be provided, or the media may have be segmented (e.g., content regions outlined 526) previously and saved as meta data in relation to the overall 3D media. A technique such as this is particularly useful when a one-to-one viewer-to-display relationship exists.

Figure 24:
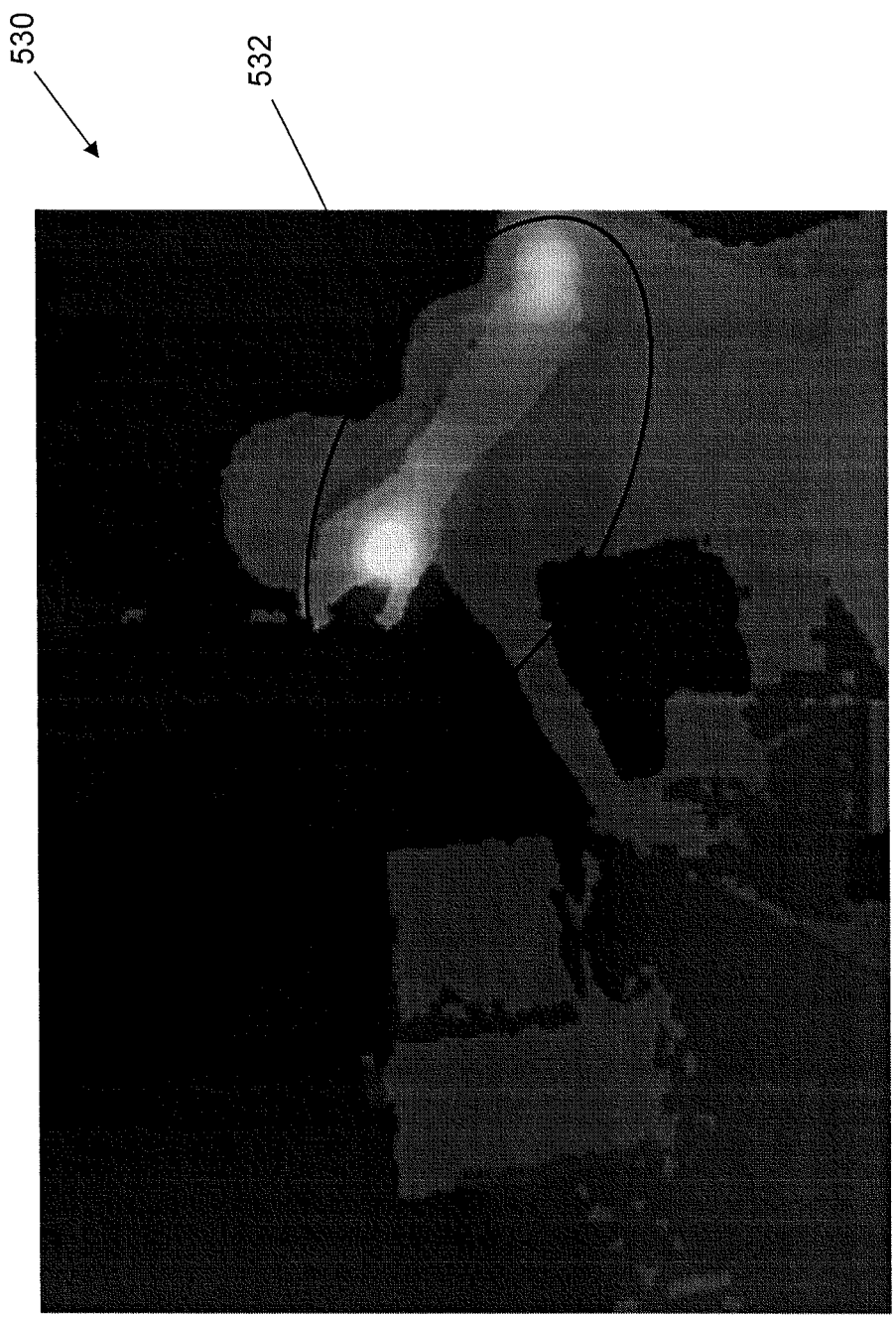
FIGS. 24 and 25 are example heat map images showing regions of 3D media content that were viewed but an incorrect depth.

As shown in FIG. 17, the VQM 46 obtained at 426 may also be used in association with media content or details thereof obtained at 428, to generate a depth output 48 at 430, e.g. by the depth output module 40. The depth output 48 can be the VQM 46 reported numerically or displayed graphically using a contour map or false colour shading to indicate the magnitude of the positive and negative depths perceived across the 3D media content 10. FIG. 24 illustrates an example of a grayscale depth image 530 which is overlaid with a heat map 532 that shows regions which were viewed but at an incorrect depth. Such a heatmap 532 may be used not only for subsequent analyses but during production of 3D media content 10, e.g., in order to allow 3D content providers 18 to edit or otherwise adjust the 3D media content 10 to improve the viewing experience based on the feedback from the heatmap 532.

Figure 25:

The depth error or mismatch between the desired depth effect and the viewer's perceived depth can be displayed as an error heatmap 536 on an image output 534, as shown in FIG. 25, wherein the hotter (whiter) temperature indicates increased error (or mismatch between actual depth and perceived depth).

The analysis module 22 can also be used in conjunction with other systems (not shown) for generating outputs related to content analysis, wherein the POG of the viewer 8 is used to determine what content is of interest, etc. For example, a system for determining content of interest could be applied to the 3D analyses being conducted. Examples of such systems may be found in U.S. patent application Ser. No. 12/727,284 filed Mar. 19, 2010, entitled "Method for Automatic Mapping of Eye Tracker Data to Hypermedia Content" published as U.S. 2010/0295774; and U.S. Provisional Patent Application No. 61/413,964 filed Nov. 15, 2010, entitled "Method and System for Media Display Interaction Based on Eye Gaze Tracking"; the contents of both applications being incorporated herein by reference.

It will be appreciated that the example embodiments and corresponding diagrams used herein are for illustrative purposes only. Different configurations and terminology can be used without departing from the principles expressed herein. For instance, components and modules can be added, deleted, modified, or arranged with differing connections without departing from these principles.

The steps or operations in the flow charts and diagrams described herein are just for example. There may be many variations to these steps or operations without departing from the spirit of the invention or inventions. For instance, the steps may be performed in a differing order, or steps may be added, deleted, or modified.

Although the above principles have been described with reference to certain specific example embodiments, various modifications thereof will be apparent to those skilled in the art as outlined in the appended claims.

The invention claimed is:

1. A method of analyzing three dimensional (3D) media content, the method comprising:
    obtaining point of gaze (POG) information from an eye tracking system;
    determining a vergence value using the POG information;
    comparing the vergence value to depth data associated with at least one object in the 3D media content; and
    providing an output based on the comparing, the output comprising at least one of a control instruction for modifying the 3D media content, an indication of at least one difference between a viewed depth and a displayed depth for the at least one object, and an analysis of content being viewed.

2. The method of claim 1, wherein the comparing generates a depth error value indicative of a difference between a viewed depth and a displayed depth for the at least one object.

3. The method of claim 2, wherein the control instruction comprises an instruction for modifying the 3D media content according to the depth error value.

4. The method of claim 3, wherein the modifying comprises adjusting focus of one or more of the at least one object in the 3D media content.

5. The method of claim 4, wherein the modifying is performed while the 3D media content is being displayed for a viewer.

6. The method of claim 4, wherein the modifying is performed offline during an analysis of the 3D media content subsequent to being displayed for a viewer.

7. The method of claim 1, further comprising calibrating the vergence value.

8. The method of claim 7, wherein the calibrating comprises:
    displaying a plurality of test object at different depths in the 3D media content;
    determining a respective vergence value at each depth; and
    computing one or more calibration parameters according to the determined vergence values.

9. The method of claim 8, wherein the test objects are provided without prompting a viewer.

10. The method of claim 8, wherein the test objects are provided using a prompt provided to a viewer.

11. The method of claim 8, further comprising repeating the calibrating.

12. The method of claim 8, wherein the one or more calibration parameters comprise any one or more of a function, and a look-up table.

13. The method of claim 1, wherein the output comprises any one or more of a contour map, false colour shading, and error heatmap showing the differences between the viewed depth and the displayed depth for the at least one object.

14. The method of claim 1, wherein the POG information is a 3D value and the vergence value is obtained from a dimension of the 3D value.

15. The method of claim 1, wherein the POG information provides left eye POG and right eye POG values on a two dimensional (2D) display screen.

16. The method of claim 15, wherein the vergence value is computed by determining a relative distance between the left eye POG and right eye POG in one dimension.

17. The method of claim 16, wherein the one dimension accounts for head tilt associated with a viewer.

18. The method of claim 16, wherein a left eye x-coordinate is subtracted from a right eye POG x-coordinate, wherein an x-axis is measured along a horizontal edge of a display screen, and wherein a positive vergence value is indicative of POG further into the 3D media content then the display screen, a negative vergence value is indicative of POG between the display screen and a viewer of the 3D media content, and a zero vergence value is indicative of POG on the display screen.

19. The method of claim 1, wherein the output comprises the analysis of content being viewed.

20. The method of claim 19, wherein the analysis provides content of interest.

21. A non-transitory computer readable storage medium comprising computer executable instructions for analyzing three dimensional (3D) media content, the computer executable instructions comprising instructions for:

obtaining point of gaze (POG) information from an eye tracking system;
determining a vergence value using the POG information;
comparing the vergence value to depth data associated with at least one object in the 3D media content; and
providing an output based on the comparing, the output comprising at least one of a control instruction for modifying the 3D media content, an indication of at least one difference between a viewed depth and a displayed depth for the at least one object, and an analysis of content being viewed.

22. An electronic device comprising a processor and memory, the memory comprising computer executable instructions for causing the processor to analyze three dimensional (3D) media content, the computer executable instructions comprising instructions for:

obtaining point of gaze (POG) information from an eye tracking system;
determining a vergence value using the POG information;
comparing the vergence value to depth data associated with at least one object in the 3D media content; and
providing an output based on the comparing, the output comprising at least one of a control instruction for modifying the 3D media content, an indication of at least one difference between a viewed depth and a displayed depth for the at least one object, and an analysis of content being viewed.

23. The electronic device of claim 22, wherein the electronic device is included in a media player.

24. The electronic device of claim 22, wherein the electronic device is included in a system further comprising an eye tracking system.

* * * * *